US008505363B2

(12) United States Patent
Masek (10) Patent No.: US 8,505,363 B2
(45) Date of Patent: Aug. 13, 2013

(54) CYCLONIC SENSOR FOR MULTIPHASE COMPOSITION MEASUREMENT

(76) Inventor: Vlastimil Masek, St. John's (CA)

( * ) Notice: Subject to any disclaimer, the term of this patent is extended or adjusted under 35 U.S.C. 154(b) by 438 days.

(21) Appl. No.: 12/955,445

(22) Filed: Nov. 29, 2010

(65) Prior Publication Data

US 2011/0146413 A1    Jun. 23, 2011

Related U.S. Application Data

(60) Provisional application No. 61/264,765, filed on Nov. 27, 2009.

(51) Int. Cl.
*G01N 37/00* (2006.01)
(52) U.S. Cl.
USPC .......................................... 73/61.44
(58) Field of Classification Search
USPC .......................................... 73/61.44
See application file for complete search history.

(56) References Cited

U.S. PATENT DOCUMENTS

| 5,028,318 A * | 7/1991 | Aslin | 210/85 |
| 2010/0319463 A1* | 12/2010 | Richardson | 73/861.11 |
| 2011/0001045 A1* | 1/2011 | Richardson | 250/286 |

* cited by examiner

*Primary Examiner* — Hezron E Williams
*Assistant Examiner* — Rodney T Frank
(74) *Attorney, Agent, or Firm* — Bereskin & Parr LLP/S.E.N.C.R.L., s.r.l.

(57) ABSTRACT

This invention relates to a cyclonic sensor chamber and a multiphase composition meter employing a sensor array compatible with such a sensor chamber. The sensor geometry imparts centripetal force to radially stratify a multiphase composition, and permits radial measurement of the entire flow composition in a linearly independent manner at different regions within the sensor. An appropriate array of sensors may be chosen to measure the properties of the composition from the group of testable composition properties consisting of speed of propagation of ultrasonic waves; amplitude modulation or attenuation of ultrasonic waves, X-rays, gamma rays, microwaves, infrared, visible and ultraviolet light; phase modulation or standing wave resonance of ultrasonic waves and microwaves; spin states of nuclei of nuclear magnetic resonance; and complex impedance, capacitance, inductance, mutual inductance, conductance, frequency response and phase delay. The sensor may be used to measure the water cut in an oil-well flow.

20 Claims, 10 Drawing Sheets

CYCLONIC SENSOR FOR MULTIPHASE COMPOSITION MEASUREMENT

FIELD OF INVENTION

The present invention relates to a device for measuring the composition of a multiphase flow, in particular for mixtures of oil, water and/or gas, and their emulsions in oil and gas extraction.

BACKGROUND OF THE INVENTION

Multiphase fluids refer to compositions of one or more materials, each potentially in different states of solid, liquid and gas and potentially in partially dissolved or immiscible states, which are also referred to as multiphase flows when flowing through a system. Multiphase flows/fluids are widely present in many processes ranging from food to petrochemical industries. Multiphase composition metering is an emerging technology that has a high potential, especially in the oil and gas industry.

Traditionally, the multiphase composition measurement in the oil and gas industry is conducted periodically (often based on regulatory requirements), on the scale of days or weeks. This measurement is performed by selecting and routing a single well stream from the production field into a test separator that separates the multiphase flow into single phase streams, and it is these single phase streams which are then analyzed. This long-standing practice has been the standard for decades but has become increasingly prohibitive in optimized production allocation systems that must react in real-time to changes in well stream compositions across the production field. As a result, there is a need for "real-time" multiphase meters which are capable of measuring multiphase composition either within the flow or at least without the need to disrupt the streams.

There have been some developments in this field. Framo Engineering developed and field tested a multiphase meter targeted for subsea installations that employed gamma-ray attenuation sensing and a cross-correlation to calculate phase fractions. However, the requirement to pre-mix the input stream leads to a less robust solution and less useful production output. Multiphase meters must reliably operate under a range of unpredictable multiphase flow conditions such as plug or slug flow. Existing multiphase meters, including the Framo meter, often use a mixer to yield a homogenous mixture essential for the accurate measurement. However, mixing complicates any downstream separation process, as fine multiphase mixtures prove difficult to separate without using additional chemicals.

Framo Engineering together with Schlumberger have also developed a meter that employs high-frequency gamma-scanning at different power levels to mitigate the criticality of mixing. But the system remains complex.

There remains a desire for a multiphase meter which has a simplified design and which can determine the composition of a production stream of fluid in an industrial process. References to oil/gas flow are for convenience, and are not meant to limit the applicability of this invention to other industrial processes involving suitable mixed composition flows.

There is a desire for such a system which does not require a nuclear particle emitter and detector or unnecessary mixing of the composition, but which may also be compatible with such a system.

Various types of probes are currently used in multiphase analysis. For example, capacitive sensors robustly operate in many industrial sensing applications such as level measurement, proximity/position sensing, product quality detection (synthetic yarn) and many others. The capacitive or electrostatic technique has been applied to multiphase flow measurement but existing applications do not effectively address wide varieties of multiphase flow regimes.

In 1988, Van der Linden, "Capacitive Sensors: Design and Applications", Wiley-IEEE Press (1996), pp. 133 (Ch. 9.5 Water/Oil Mixture Probe), ISBN-13: 978-0780353510 ("Van der Linden") developed an oil-water percentage probe for water contaminated oil streams. The method employed an AC bridge with a temperature compensated oil dielectric reference. The signal conditioning eliminated the effects of parasitic capacitance by using low-impedance amplifiers and the probe featured good accuracy. However, the system was not applicable to a wide range of oil-water percentages, the mixture needed to be homogenous, and drifting of the dielectric constant beyond the temperature linked drifts from the oil dielectric reference cannot be detected by this method. The presence of an externally powered pump that circulates the oil reference adds system complexity and power inefficiency.

A variety of capacitance sensors for determining volume fractions in two-phase pipelines were researched by Abouelwafa and Kendall, "The Use of Capacitance Sensors for Phase Percentage Determination in Multiphase Pipelines", Abouelwafa, M. Sami A.; Kendall, E. John M.; Instrumentation and Measurement, IEEE Transactions on Volume 29, Issue 1, March 1980 Page(s): 24-27 ("Abouelwafa et al.").

In Abouelwafa et al., concave plate electrodes affixed internally and externally to a pipe were compared in sensing a fluid's permittivity and conductivity. A measurement of complex impedance, or simply conductance and capacitance has also been examined as a possible proxy for determining multiphase composition ratios. However, this research did not address changes in the properties of the flow, and there remains a need to develop a sensor capable of multiphase measurement where phase properties or temperatures of the materials drift.

Multiphase flow measurement requires the knowledge of flow rates of individual phases or the total multiphase flow rate in $m^3$/sec or gal/min and the composition. The composition is defined as the volumetric ratio of individual phases against the total tested volume. In the Oil & Gas industry for example, the best case scenario is pumping 100% hydrocarbons and 0% water, which is rarely the case. However, the worst case scenario of pumping 100% 'produced water' is also rare. Therefore, ideally, the composition ranging from 0% to 100% must be considered. Note that the extreme 0%/100% composition actually constitutes a single phase flow.

Additional problems exist in the prior art in relation to: measuring all possible composition ratios of a multiphase fluid, i.e. 0% to 100% of all fluids; and where a homogeneous mixture is not required, reliable stratification of the flow for the purposes of measurement. The prior art identifies horizontal stratification pipes, which are unreliable in high flow rate applications, or large-size expensive separators used to slow down the stream significantly. Where one phase is conductive, gravity based stratification may be amplified using an electromagnetic field, but the large power consumption, complexity and, in the case of combustible fluids, danger, in this approach make it highly impractical.

For known horizontal stratification pipes of rectangular cross section, whether they operate as parallel capacitors or series capacitors, linearly independent measurements of the flow cannot be obtained by changing the aspect ratios of the pipes, only by selectively omitting to measure part of the flow. Since additional measurements are needed for each additional parameter (unknown) of the flow, it quickly becomes difficult to solve for more than two variables without greatly restricting the composition fractions which can be measured.

There is a need for a multiphase sensor which is able to operate in the full measurement range, with improved stratification of the phase layers, and which is capable of operating with a variety of metrics.

SUMMARY OF THE INVENTION

The present invention is a multiphase meter using a novel cyclonic sensor chamber having a plurality of measurement regions of differing cross-sectional shape, such that measurements along (i) a diameter or (ii) radially from a core, within the chamber are linearly independent in respect of stratified layer boundary depths. A sensor array positioned at the plurality of measurement regions is capable of operating on production flows of multiphase compositions to obtain real-time measurement of the ratios and properties of the composition. In the oil/gas context, the sensor determines the proportions of oil, gas, water, and other features of the multiphase composition using measurements of at least one property of the composition which measurements are linearly independent across flows of different cross sectional areas within a locally radially stratified flow. Many properties of the fluids/compositions under study may be suitable for this purpose, including possibly, speed of propagation of ultrasonic waves; amplitude modulation or attenuation of ultrasonic waves, X-rays, gamma rays, microwaves, infrared, visible and ultraviolet light; phase modulation or standing wave resonance of ultrasonic waves and microwaves; spin states of nuclei of nuclear magnetic resonance; and complex impedance, capacitance, inductance, mutual inductance, conductance, frequency response and phase delay (collectively referred to as the "testable properties", the fluid "parameters" or the fluid or flow "properties"). In one generalization of the invention, the radial distances to stratified fluid boundaries in a cyclonically stratified flow (i.e. the individual fluid depths measures from the centre of the cross section or across the entire diameter). As radial distances determine volume for a given chamber shape, these equations easily solve for volumetric ratios for differently shaped portions of the sensor chamber. Different shapes are achieved by narrowing the chamber (a funnel shape, which also increases the centripetal forces) or adding a central core (giving the cross section a donut shape).

The invention avoids the complexity of prior systems by featuring a sensor array embedded within a cyclonic phase stratifier. A system of the proposed invention is fully scalable to meet the size of an entire flow, and when implemented using a sensor array capable to measuring any of the testable properties, has a provision for added robustness. In addition to the volumetric fraction sensing, more insight into individual phase properties can be achieved. As evidence of the robustness, in the case of capacitive sensor probes, insight into various material properties (including temperature) can be gained through correlation with the phase dielectric constants and extracted in the same measurement. Additional robustness may be gained by exploiting the simultaneous measurement of different properties, including fluid dielectric properties or magnetic susceptibility. Finally, a meter implemented using the radially/cyclonically stratifying sensor chamber can also distinguish between separable multiphase flow conditions and emulsions that are inseparable by simple means, by solving for such conditions and emulsion properties using additional measurements.

In one aspect, the invention is characterized by radial stratification of the multiphase flow within the sensor chamber by the centripetal forces imparted on the fluid by its flow through the appropriately shaped sensor chamber. In another aspect, the invention is characterized by the combination of: (A) a cyclonic sensor chamber (possibly with a concentrically positioned central core) disposed to collect the multiphase flow being measured in a manner to impart centripetal forces on the flow (possibly by having the input flow approximately tangential to the wide end of the funnel shaped sensor chamber, causing the fluid to flow as a cyclone through the funnel and out the narrower end of the sensor), radially stratifying the fluid within the sensor chamber, with (B) an array of sensor probes (determined by the type of sensor used) positioned to measure one or more composition or flow properties across the full span of potential multiphase composition $\overline{\alpha}$ (where the vector $\overline{\alpha}$ represents the ratio of the volumes of individual phase components to the total volume) either from a central core to the sensor chamber outer wall or diametrically across the entire fluid, in separate regions of the sensor chamber where the geometry of the chamber and the flow render the measurements linearly independent. In the case of a sensor measuring capacitance or mutual inductance, an electrode array or coil array may be used. Such an array may be further characterized as electrodes (plate, concentric rings or mutual inductance coils) positioned such that the entire flow passes between them.

The approach of the current invention is to utilize the kinetic energy of the multiphase flow plus gravity in a cyclonic phase stratifier, a cyclone in brief. The stream is directed tangentially into the wide end of a funnel shaped chamber, where it rotates in a helical spiral as it flows towards an output, thus creating large centrifugal forces that (optimally combined with gravity) separate the phases by density.

These centrifugal forces increase as the rate of flow of the composition through the sensor chamber increases. Therefore, in order to increase the centrifugal forces stratifying the fluids measured by the sensor or to maintain a constant flow rate across the sensor, the flow rate may need to be locally increased or buffered through the use of a recirculating pump.

In the example where the cyclone is instrumented with a capacitive sensor array, the determination of multiphase flow composition can be reduced to a relatively simple set of equations that is less constrained than in the prior art. This approach may be extrapolated to speed of propagation of ultrasonic waves; amplitude modulation or attenuation of ultrasonic waves, X-rays, gamma rays, microwaves, infrared, visible and ultraviolet light; phase modulation or standing wave resonance of ultrasonic waves and microwaves; spin states of nuclei of nuclear magnetic resonance; and complex impedance, capacitance, inductance, mutual inductance, conductance, frequency response and phase delay; or any other testable properties of the composition which vary in relation to the amount of the fluid to be traversed.

Preferably, the electrode or coil array comprises a plurality of sensor regions, where each sensor region is comprised of (1) an inner ring of conductive material or coil about the inner wall at a given height along the axis and (2) an outer ring of conductive material or coil about the outer wall being closest to such inner ring. In an alternative embodiment, the inner or outer ring in a sensor region may be subdivided into a plurality of electrodes (conductive material or coils or a combination). (It is within the scope of the invention to consider "rings" which are not necessarily cylindrical, but which conform to the inner wall and outer wall.) Alternatively, the entire inner wall or the entire outer wall may be a conductor or coil connected to a common voltage or ground, so as to simplify sensor analysis.

In a further alternative, the sensor array may be replaced with mutual inductance coils positioned in pairs or triplets at each measurement location of the array resembling an LVDT (linear variable differential transformer) that has an additional capacity of measuring the speed of flow without the need for the flow to pass a constriction (orifice, Venturi tube).

The available shapes of sensor chambers of the present invention are based on known surfaces of rotation about a chamber axis. The inner wall of the concentric core and the chamber wall of the sensor chamber itself, can be modelled in a variety of ways as shown in the Figures, and multiple sensors can be concatenated and used in series to provide additional measurement within the scope of invention. As the chamber wall exerts the centripetal force on the fluid, its shape (i.e. its "known curvature") is of principal concern in the design of sufficient centripetal force. The inner wall is typically designed for either desirable fluid depth measurements (which depend on the parameter or testable property being measured) and/or substantially constant cross sectional area across the direction of flow to avoid turbulence. Ideally, the flow is cyclonic about the chamber axis, but generally along the axis from the chamber input to the chamber output.

It is an object of the present invention to create "real-time" multiphase meters which are capable of measuring multiphase compositions either within the flow or at least without the need to disrupt the streams. The sensor chamber design is scalable, and can be designed in accordance with the present invention to accept all, or any portion, of the multiphase composition and take linearly independent measurements of a testable property (as defined above) across the entire accepted portion of the flow, in one step, without the need to halt the flow.

It is an object of the present invention to create a cyclonic sensor chamber of simplified design to permit the radial/cyclonic stratification of a multiphase fluid in manner which permits measurement of the fluid during stratification.

It is an object of the present invention to create a cyclonic sensor array using passive or low voltage components and (where input velocity of the fluid is sufficient) no moving mechanical parts.

It is an object of the present invention to create a multiphase sensor for the oil and gas industry which does not require nuclear particle emitters, nuclear particle detectors, external pumps or stratification of the flow using magnetic fields, but is compatible with such devices.

It is an object of the present invention to use the linear independence of the system and assumptions arising from calibration and geometry to determine flow phase properties, temperature and other parameters so as to permit multiphase measurement where phase properties, temperatures or other parameters of the materials drift during sensor operation.

It is an object of the present invention to create a multiphase meter that is self-calibrating.

It is an object of the present invention to create multiphase meters capable of measuring the entire range of relative volumes of phases within a composition.

There can also be situations, largely in 'channel' type flow regimes of liquids and gases, where individual phases travel at different speeds. Configuring the sensor to determine fluid velocity is within the scope of invention, as is using a recirculating pump to increase flow rate or maintain constant flow rate. The novel use of a cyclonic sensor and the measurement of fluid properties across a radially stratified flow is within the scope of invention. The solution of equations for the preferred embodiments discussed below is merely one possible configuration for use in the Oil & Gas industry and is not meant to be limiting in any respects. The calculations and assumptions regarding the near equal velocity of mixed liquids in a multiphase flow are made for explanatory purposes only. It would be within the scope of the invention to use table look up values for testable properties rather than direct calculations, provided that the same physical phenomena are used to create linearly independent measurements across a radially stratified flow. As such, the discussion below relates principally to the ratio of produced water compared to the volume of total liquids produced in an Oil and Gas extraction process, the so called 'watercut', but may be useful in other industrial processes where knowledge of the volumetric ratios of multiphase compositions is desirable.

DETAILED DESCRIPTION OF THE INVENTION

Certain embodiments of the present invention will now be described in greater detail with reference to the accompanying drawings.

Figure 1:
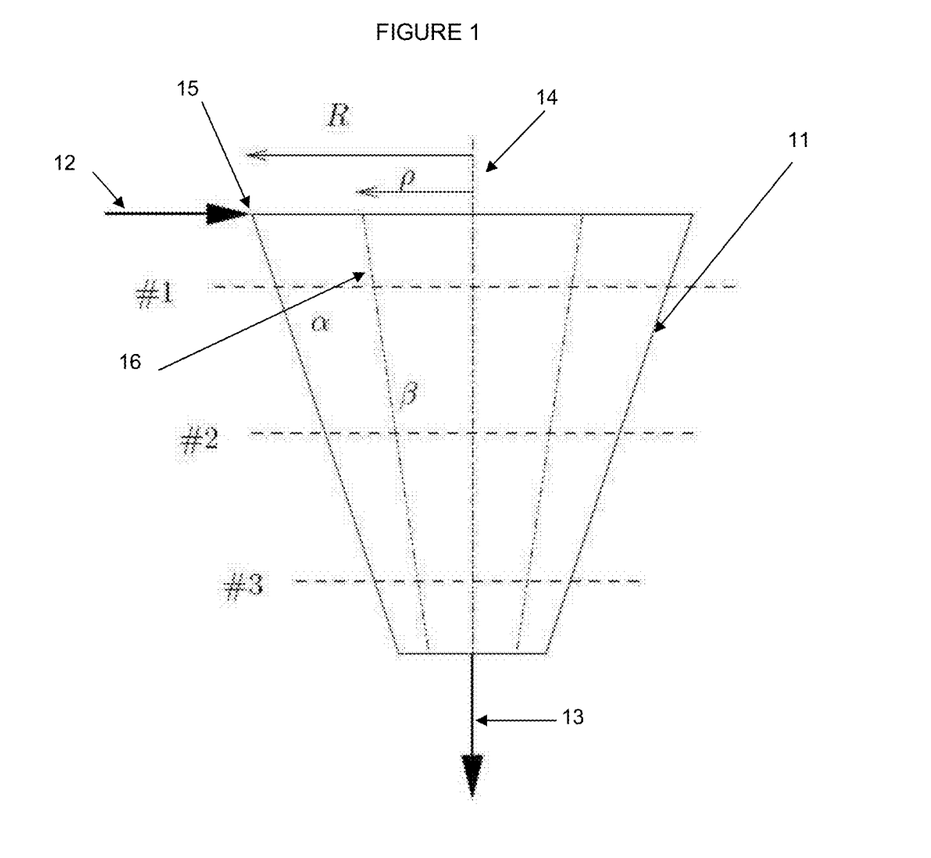
FIG. 1 is a cross-sectional view of a funnel shaped sensor chamber of the present invention without a core, as a hollow cyclone.

FIG. 1 shows the general principal of the invention as a cross sectional view of a funnel shaped sensor chamber (11). A multiphase fluid flowing in the direction of the thick input arrow (12) enters the sensor chamber (11) of radius R about an axis (14), and the flow about the axis (14) induces cyclonic motion of the fluid as flows around the inner surface (15) until it passes through the output (13). The centripetal forces of the cyclonic motion encourage stratification of the multiphase fluid, with the less dense fraction (identified by β) disposed towards the center and the denser fraction (identified by α) disposed towards the surface (15) of the funnel shaped sensor chamber (11). Ideally, a sensor chamber input (12) is oriented to encourage cyclonic motion of the fluid as it enters the sensor chamber. The curvature of the sensor chamber is also designed to impart the appropriate amount of force. At each of planes, #1, #2 and #3, measurement of the radial distance ρ, defined by the boundary (16), which determine the areas occupied by β as a function of R (and therefore the composition), are linearly independent. The radial distance ρ can be measured either across the diameter of the funnel (11) in each of the planes, #1, #2 and #3, or from a sensor located along the axis of the sensor chamber towards the sensor chamber wall (11).

Figure 2:
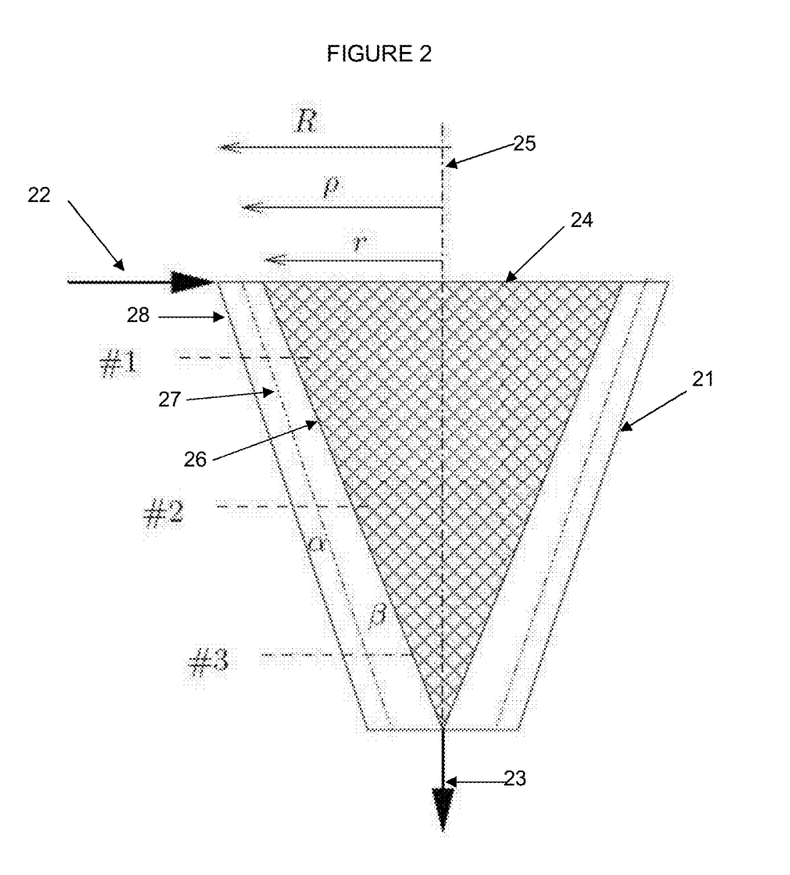
FIG. 2 is a cross sectional view of a sensor chamber of the present invention formed in the cavity between a cone and a funnel, as a cored cyclone.

FIG. 2 shows a variation on FIG. 1. In FIG. 2, as shown in cross section along the axis (25), a conic shaped surface (21) forms the outer wall (28) of the sensor chamber, in which a concentric core (24) is also disposed along the sensor axis (25), the core having a core wall (26) which forms an inner wall of the sensor chamber. The core may be selected to maintain similar total cross sectional area within the sensor chamber at each of the sensor regions in planes #1, #2, and #3. The composition to be measured flows into the sensor chamber though an input in the direction of the arrow (22), and leaves in the direction of the arrow (23), having passed in circular motion about the axis (25) and between surfaces (26) and (28) thereby generating centripetal forces within the fluid, stratifying it at a fluid boundary (27). Measuring the radial distances to this boundary (27) at planes #1, #2, and/or #3 allow robust measurement of the phase composition.

Figure 3:
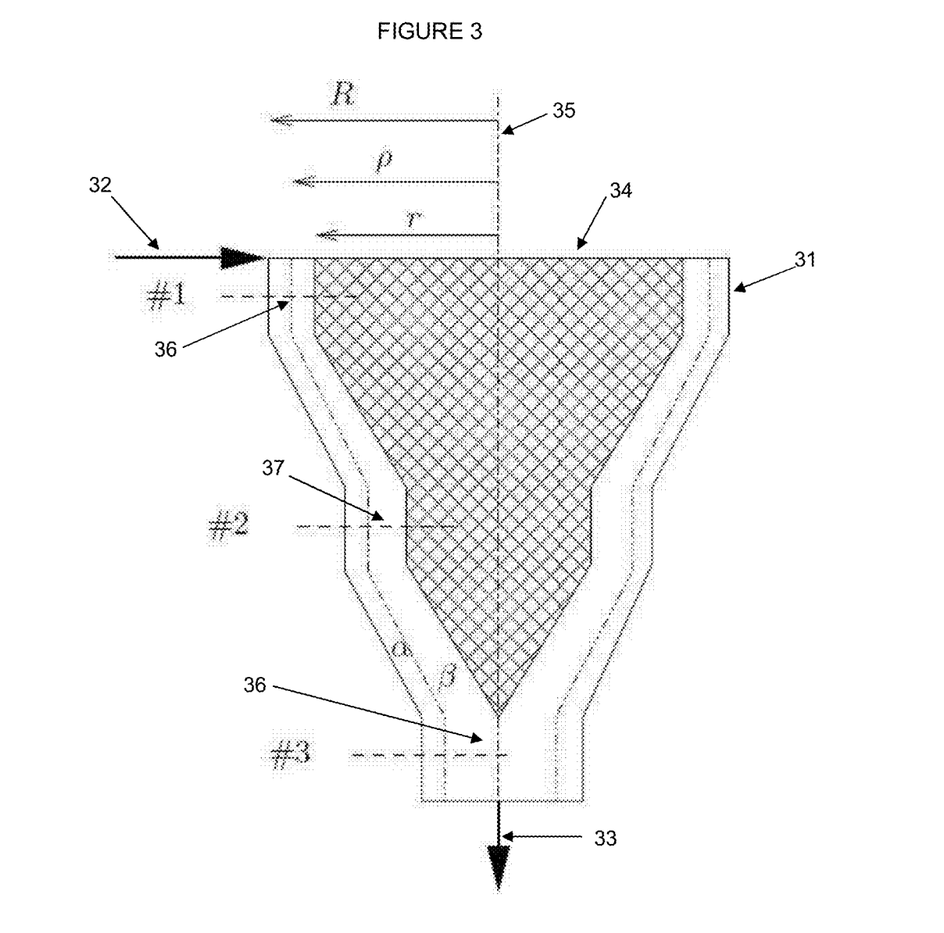
FIG. 3 is cross sectional view of a sensor chamber of the present invention formed in the cavity between an outer surface of rotation and an inner surface of rotation, in which sensor regions are concentric cylinders and the spaces between are concentric truncated cones, as a stepped cyclone.

FIG. 3 shows a design of a sensor chamber (31) of the present invention which incorporates concentric cylindrical stages (36), (37) and (38) of different inner radius r and outer radius R about axis (35) to simplify system computations at each of the sensor regions in planes, #1, #2 and #3. The inner core (34) is preferably chosen to maintain cross sectional area through the sensor chamber as fluid flows cyclonically from input (32) to output (33).

Figure 4:
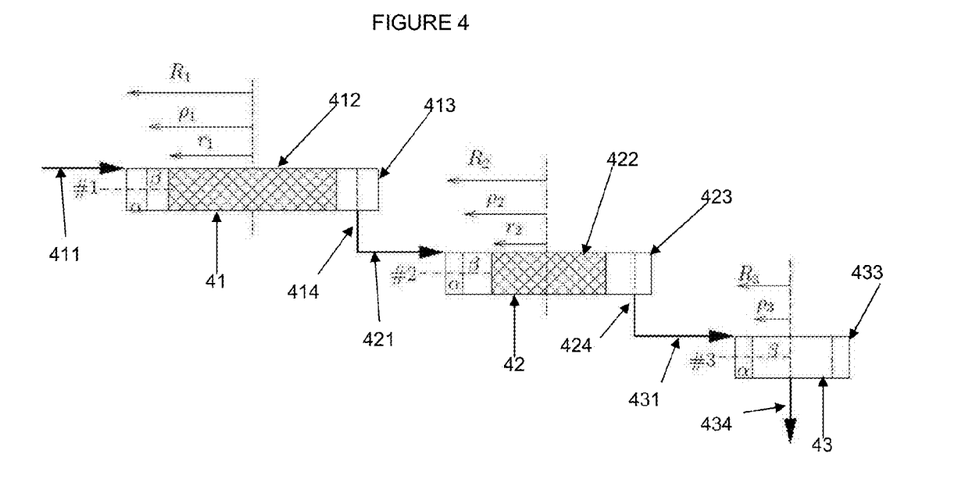
FIG. 4 is a cross-sectional view of a separate sensor bodies implemented using the cavities between an outer cylinder and an optional core cylinder, as a cascaded cyclone.

FIG. 4 shows three cascaded sensor chambers (41), (42) and (43), used to achieve the overall invention. Input (411) flows into the chamber (41) defined between inner cylindrical core (412) and outer cylindrical surface (413), and the longitudinal output (414) is feed tangentially as an input (421) to chamber (42). The chamber (42) has different inner cylindrical core (422) and outer surface (423), such that the boundaries of the stratified fluid layers will be at different ratios in chamber (42) than they are in chamber (41). The fluid exiting in the axial direction from output (424) is input to sensor chamber (43) in the tangential direction at input (431) and moves cyclonically within the surface (433) on its path through output (434). In this configuration, it is relatively simple to measure fluid parameters across the entire fluid from each inner core towards each sensor chamber wall. In the third stage, an optional cylinder without a core is shown. In each of planes #1, #2 and #3, since the pairs $(r_1, R_1)$, $(r_2, R_2)$ and $(r_3, R_3)$ are different, the equations to determine the distances $\rho_1, \rho_2,$ and $\rho_3$, of the fluid boundary from the axis of the sensor are linearly independent for a fluid of composition (α, β).

Various parameters of the stratified multiphase flow (i.e. the testable properties) can be measured as proxies for the fluid boundary location, including: those multiphase flow properties from the group of multiphase flow properties consisting of: speed of propagation of ultrasonic waves; amplitude modulation or attenuation of ultrasonic waves, X-rays, gamma rays, microwaves, infrared, visible and ultraviolet light; phase modulation or standing wave resonance of ultrasonic waves and microwaves; spin states of nuclei of nuclear magnetic resonance; and complex impedance, capacitance, inductance, mutual inductance, conductance, frequency response and phase delay.

A multiphase flow stratified in cyclone device(s) of varying diameter such as ones in FIGS. 1, 2, 3, 4 results in non-linear radii mapping with respect to a "constant" composition; a constant composition being one where the ratio $(R\_i^2)/(\rho\_i^2)$ is constant across the measure for a given composition but the ratio $R\_i/\rho\_i$ is not—or at least where the second ratio is not linearly related to the first. This can be efficiently utilized in a robust composition measurement under parameter drifting conditions such as temperature, speed of propagation, reflection/refraction indexes, electrical impedance (including permittivity and permeability) and others. Examples of possible embodiments of this technique utilizing different detection methods are listed in the tables below. FIGS. 1 through 4 show a two-phase flow (phases α and β) being measured at three different locations (#1, #2 and #3) in order to determine two parameters plus the composition. For example, in case of an acoustic impedance method utilizing the Time-Of-Flight measurement, the speed of sound propagation in phases α and β and the composition can be measured this way. If only the composition is needed, the measurement is compensated against adverse effects of parameter drifting such as the temperature.

Chart 1: Signal Medium Employing Indirect Sensing Principle and Sensor Chamber Compatibility:

| Signal Medium | Indirect Sensing Principle | | |
|---|---|---|---|
| | Speed of Propagation; Time-of-Flight | Amplitude Modulation Attenuation | Phase Modulation Standing Wave Resonance |
| Ultrasonic | FIGS. 1, 2, 3 or 4 in transmission or reflection mode | FIGS. 1, 2, 3 or 4 in transmission or reflection mode | FIGS. 1, 2, 3 or 4 in transmission or reflection mode |
| X-rays, Gamma Rays | | FIGS. 1, 2, 3 or 4 in transmission mode | |

-continued

| Signal Medium | | |
|---|---|---|
| Microwaves | FIGS. 1, 2, 3 or 4 in transmission or reflection mode | FIGS. 1, 2, 3 or 4 in transmission or reflection mode |
| IR; Visible, UV | FIGS. 1, 2, 3 or 4 in transmission mode, but cannot penetrate opaque fluids well. | |
| | Spin States of Nuclei | |
| NMR | FIGS. 1, 2, 3 or 4, but phases must differ in Larmor frequency; e.g. hydrocarbons and water. | |

Chart 2: Signal Medium Employing Direct Sensing Principle and Sensor Chamber Compatibility:

| Direct Sensing Principle | | |
|---|---|---|
| Capacitance | Inductance | Conductance |
| FIGS. 1, 2, 3 or 4; also in combination with the conductance measurement | FIGS. 1, 2, 3 or 4 in self and/or mutual inductance measurement | FIGS. 1, 2, 3 or 4; also in combination with the capacitance measurement; can result in short circuiting if high conductivity phase such as water in dominant. |

By way of example only, and without limiting the generality of the foregoing, in a preferred embodiment of the present invention for use in the oil and gas industry, as described in FIGS. 5 through 12, capacitance of a radially stratified oil-water mixture can be measured using the present invention to determine the water-cut.

A key design consideration is designing the sensor with appropriate metrics for the testable properties and electrode geometries to facilitate accurate measurement. The solution of a large group of problems in electrostatics is to find a potential distribution that satisfies the Laplace equations with given electrode geometry and electrode voltages. What follows are the design criteria in the capacitive domain. Other assumptions may be used in other measurement domains on other testable properties (as noted in the charts above), without limiting the scope of the sensor and system of the present invention. Where capacitance is the chosen testable property, in order to analytically derive the capacitance between the pairs of electrodes in the array, we consider the following assumptions
1. Electric fields inside the conductors are negligible due to small current flows (the conductor surface is an equipotential surface).
2. The boundary between two dielectrics is an equipotential surface (the single two-dielectric capacitor can be dissected into two capacitors of single dielectric that are connected in series).
3. Electrodes added in the practical system to act as shields or guards to control fringing flux, reduce unwanted stray capacitance and shield against unwanted pickup of external electric fields can be added to improve measurement, but are not directly considered.
4. The availability of such known design elements is assumed, such that fringe capacitance and stray capacitance is ignored.
5. Unwanted capacitive coupling between multiple electrode pairs, the crosstalk, is similarly ignored.

It would be readily apparent to a person of skill in the art how to appropriately solve for other testable parameters.

In addition to the above assumptions, we consider the cyclonic stratifier design meeting the condition that the cross-section area perpendicular to the flow velocity vector is constant inside the measurement chamber. This requirement is not completely necessary for the proper function of the multiphase meter, but stabilizes the flow velocity and the multiphase flow regime properties within the multiphase meter. In practice, an optional recirculating pump may be used to both increase flow rate through the sensor chamber (thereby increasing the centripetal forces which stratify the composition into its phases) and to stabilize the flow velocities (thereby preserving the assumptions above).

To demonstrate implementation of the generalized invention, two analytical models to verify the multiphase meter's feasibility are presented. In the sensor (500) shown in FIG. 5, small segments of cylindrical electrodes, shown in pairs (56), (57) and (58),(59), are considered as planar parallel-plate capacitors on the outer surface (51) and inner surface (52), which defines the sensor chamber volume (50). The objective of the first model is to show the non-linear distribution of the dielectric boundary (60) across the array elements $C_1$ and $C_2$ that translates into the required set of linearly-independent equations. In the sensor (100) shown in FIG. 10, more realistic concentric cylindrical electrode pairs (111), (112) and (113),(114) are considered to show an additional nonlinearity that translates into increased measurement robustness. The sensors in FIG. 5 and FIG. 10 are also geometrically adjusted such that the funnel shape cyclone has concentric cylindrical electrodes in regions #1 and #2.

Figure 5:
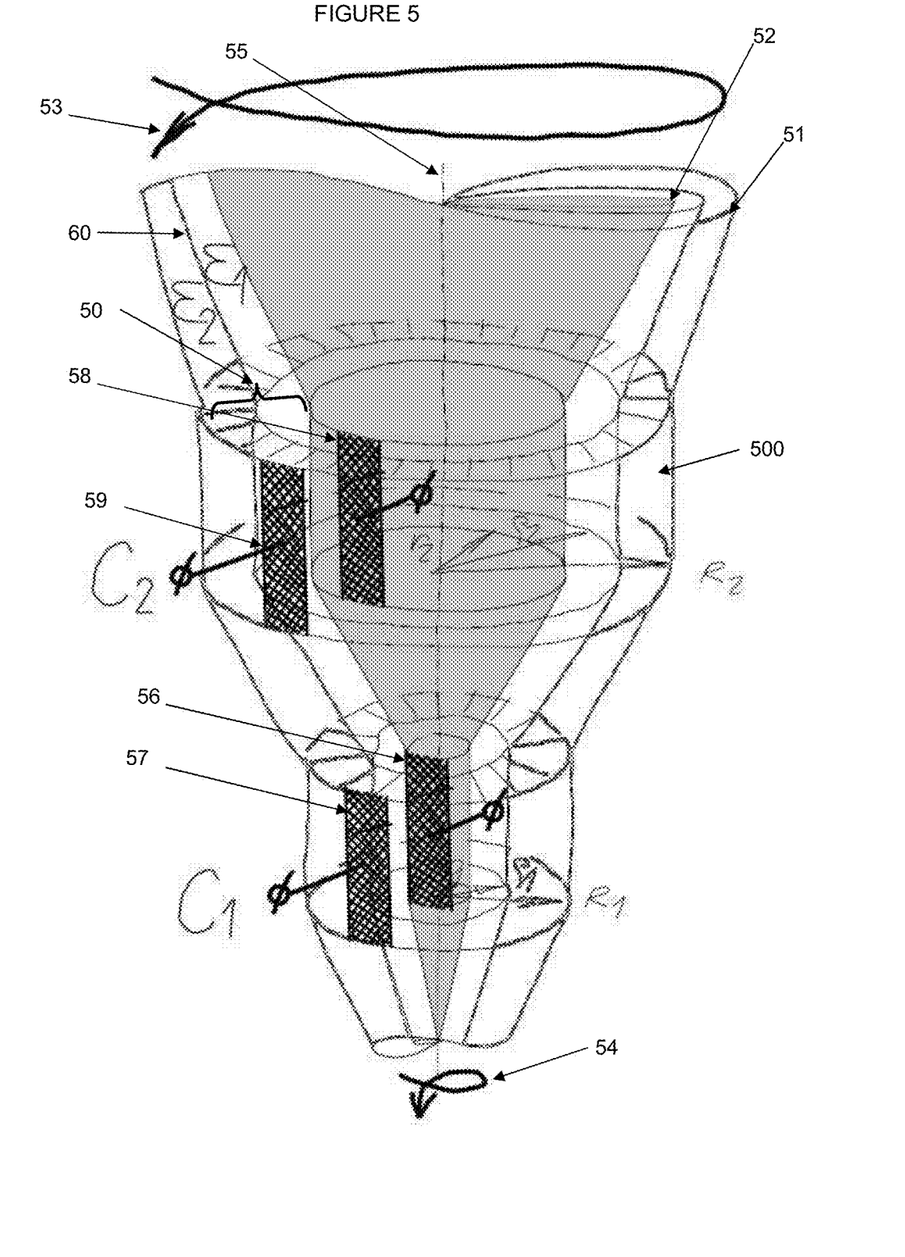
FIG. 5 is a semi-transparent perspective view of the multiphase meter of the present invention implemented using parallel plate electrodes.
Figure 6:
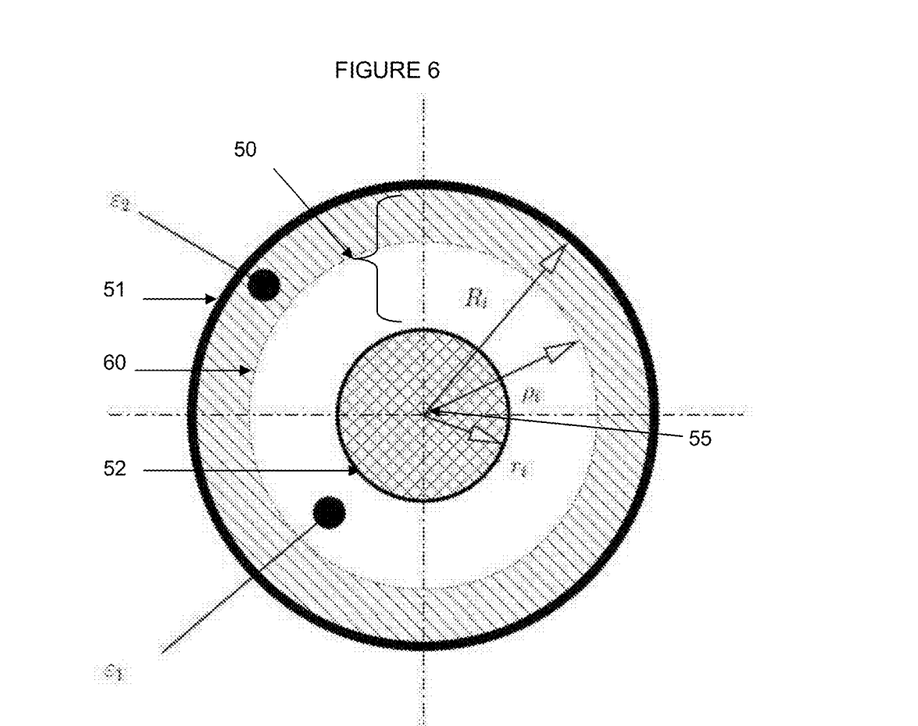
FIG. 6 is a cross sectional view of the sensor of FIG. 5 at a point "i" along the axis of rotation of the cyclone.
Figure 10:
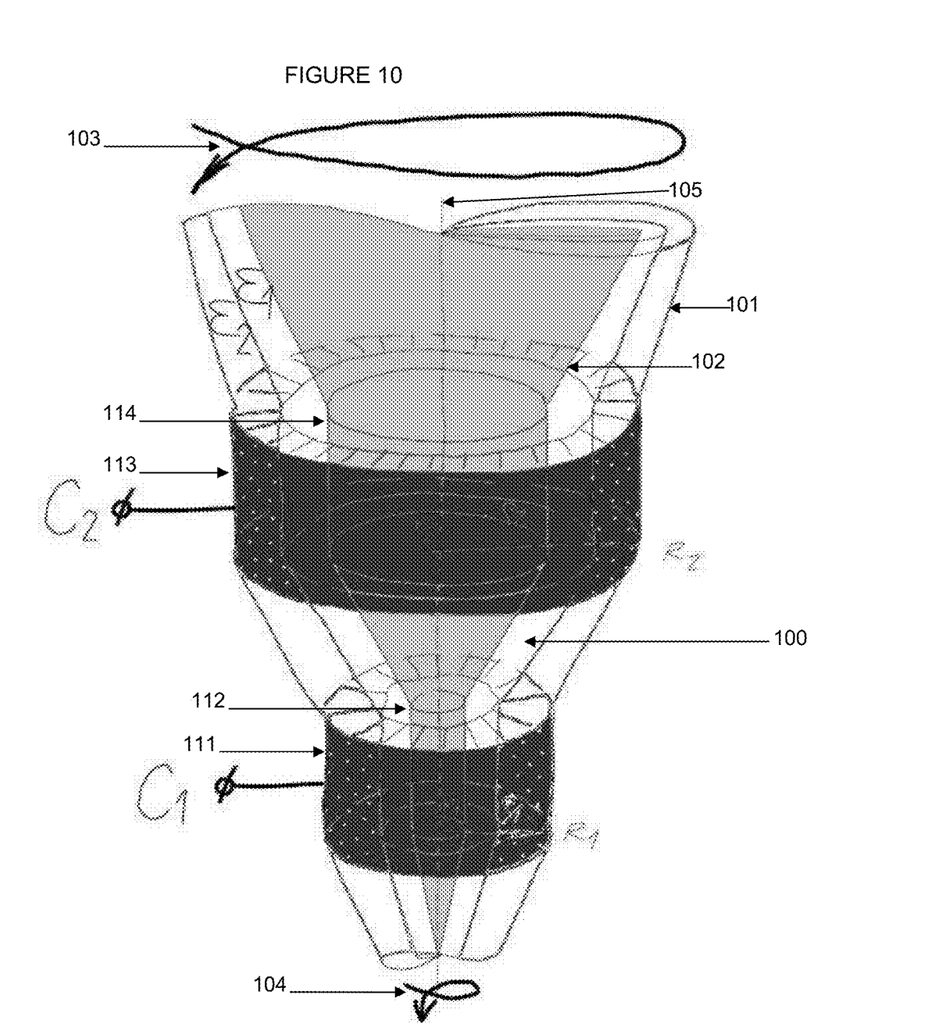
FIG. 10 is a semi-transparent perspective view of a multiphase meter of the present invention implemented using the sensor chamber of FIG. 5 and concentric cylinder electrodes.

In each of FIGS. 5, 6 and 10, the oil-water mixture (a multiphase fluid) has been stratified by cyclonic flow though a sensor chamber defined by inner wall radius $r_i$ from the axis of rotation and outer wall radius $R_i$ from the axis of rotation such that the multiphase composition is divided into a first less dense material with dielectric constant $\in_1$ and a second more dense material with dielectric constant $\in_2$. In the sensor regions of the examples depicted, the sensor chamber resembles concentric cylinders, and for demonstration purposes, the 2 sensor regions determine, respectively, capacitances $C_1$ and $C_2$ based upon phase permittivities $\in_1$ and $\in_2$ (which may have also been determined by more or more sensors of the present invention) and the regions' respective inner and outer radii $r_1$ and $R_1$ and $r_2$ and $R_2$, in order to determine, inter alia, $\rho_1$ and $\rho_2$—and the ratios of materials in the multiphase composition (in this example, the water-cut).

In FIG. 5, the two-phase fluid has been stratified within the sensor (500) by input motion (53) in a cyclonic direction about axis (55) until output (54). Region #1 between plates (56) and (57) defines a separate sensor geometry from that of Region #2 between plates (58) and (59). As such, the location of the boundary (60) between the lighter inner fluid with permittivity $\in_1$ and the heavier outer fluid with permittivity $\in_2$, can be determined as set out below.

FIG. 6 shows a generalized cross-section "i" of the sensor of FIG. 5. The sensor chamber (50) is the region formed between two known surfaces of rotation: an inner wall (52) of the chamber (50) which is the surface of the central core with radii $r_i(y)$ about an axis "y" (55); and an outer wall (51) of the chamber (60) which is the inner surface of a larger volume of rotation with radii $R_i(y)$ about the same axis "y". The measurements of one or more of the testable property are taken between a sensor on the inner wall (52) and a corresponding sensor on the outer wall (51) in a sensor region "i". Multiple sensor chambers of the present invention (each measuring across different $(r_i(y), R_i(y))$ regions "i" may be concatenated along the same flow to provide linearly independent measurements of one or more of the testable properties to the meter, and permit determination of even more flow parameters. By setting the parameter $r_i(y)$ equal to 0, the analysis reduces to a sensor chamber without a core. When the composition passing through the sensor chamber is two separable fluids $\in_1$ and $\in_2$, the boundary (60) between those fluids can be calculated through the sensor readings over multiple sensor regions "i", and solved to determine the volumetric ratios.

In another preferred embodiment, of the type depicted in FIG. 1, cone segment electrodes may be installed to mitigate flow 'bending', turbulence and discontinuities. In another preferred embodiment, one wall of the sensor chamber may be a cone, while the other side of the sensor chamber may be designed such that the cross sectional area of the total flow remains constant (so as to avoid further disrupting the flow).

As part of the design, the first approximation of the parallel plate electrode pairs assumes that the aspect ratio $$\frac{R_i - r_i}{r_i}$$

is small enough to consider the concentric cylinder electrodes (shown as (111),(112) and (113),(114), at regions #1 and #2 of FIG. 10, respectively) or their segments (shown as (56), (57) and (58),(59), at regions #1 and #2 of FIG. 5, respectively) as parallel plate capacitors. In the design of a sensor where the testable property is capacitance, since we are not concerned with the absolute capacitance but rather the relative changes across the array, the product "$\in_0 A$" of the parallel plate capacitance is set to unity.

The objective of the analysis below is to prove the sensor's working principles for which the optimized design of the cyclonic stratifier is not critical. For any dissimilar radii pair $r_1 \neq r_2$ this is a unique solution to the water-cut. By selecting three design parameters $r_1$, $R_1$ and $r_2$ a skilled user can calculate $R_2$ from the constant cross-section area condition set above as:

$$R_2 = \sqrt{\frac{A_\phi}{\pi} + r_2^2} \qquad \text{Eq. (1)}$$

where $A_\phi = \pi(R_1^2 - r_1^2)$ Eq. (2)

The electrode pair capacitance $C_1$ and $C_2$ is then calculated as $$C_i = \frac{C_i^1 \cdot C_i^2}{C_i^1 + C_i^2}, \quad i = 1, 2 \qquad \text{Eq. (3)}$$

where, $$C_i^1 = \frac{\varepsilon_0 \varepsilon_1 A}{\rho_i - r_i}, \ldots C_i^2 = \frac{\varepsilon_0 \varepsilon_2 A}{R_i - \rho_i} \qquad \text{Eq. (4)}$$

which evaluates to $$C_i = \frac{\varepsilon_0 \varepsilon_1 \varepsilon_2 A}{\varepsilon_1 (R_i - \rho_i) + \varepsilon_2 (\rho_i - r_i)} \qquad \text{Eq. (5)}$$

The composition $\alpha$, assumed constant across the array, is defined as a volumetric ratio of dielectric $\in_1$ to the total volume of dielectrics $\in_1$ plus $\in_2$, thus $$\alpha = \frac{A_{\varepsilon_1}}{A_\phi} = \frac{\rho_i^2 - r_i^2}{R_i^2 - r_i^2}, \quad i = 1, 2 \qquad \text{Eq. (6)}$$

from which the formula for the dielectric interface radius $\rho_i$ in terms of $\alpha$ is derived as $$\rho_i = \sqrt{\alpha(R_i^2 - r_i^2) + r_i^2}, i=1, 2 \qquad \text{Eq. (7)}$$

In an embodiment of the present invention for sensing a water-oil mixture, the watercut ($\in_2$ phase) is obtained as $\alpha_w \% = 100\% - \alpha \%$, for example.

Both capacitances $C_1$ and $C_2$ can then be expressed in terms of permittivities $\in_1$ and $\in_2$ and the composition $\alpha$ by substituting Eq. (7) into Eq. (3):

$$C_i = \frac{\varepsilon_0 \varepsilon_1 \varepsilon_2 A}{(\varepsilon_2 - \varepsilon_1)\sqrt{\alpha(R_i^2 - r_i^2) + r_i^2} + \varepsilon_1 R_i - \varepsilon_2 r_i} \qquad \text{Eq. (8)}$$

Figure 7:
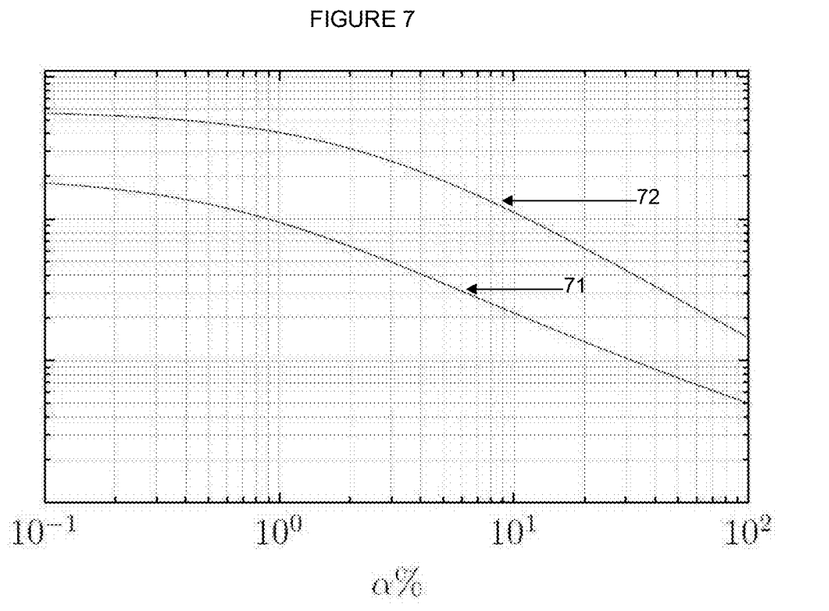
FIG. 7 is a logarithmic plot of capacitances for two sensor regions of the multiphase meter of FIG. 5, as a function of composition, where the ratio of the inner radius of the first sensor region to the inner radius of the second sensor region is 1:8.
Figure 8:
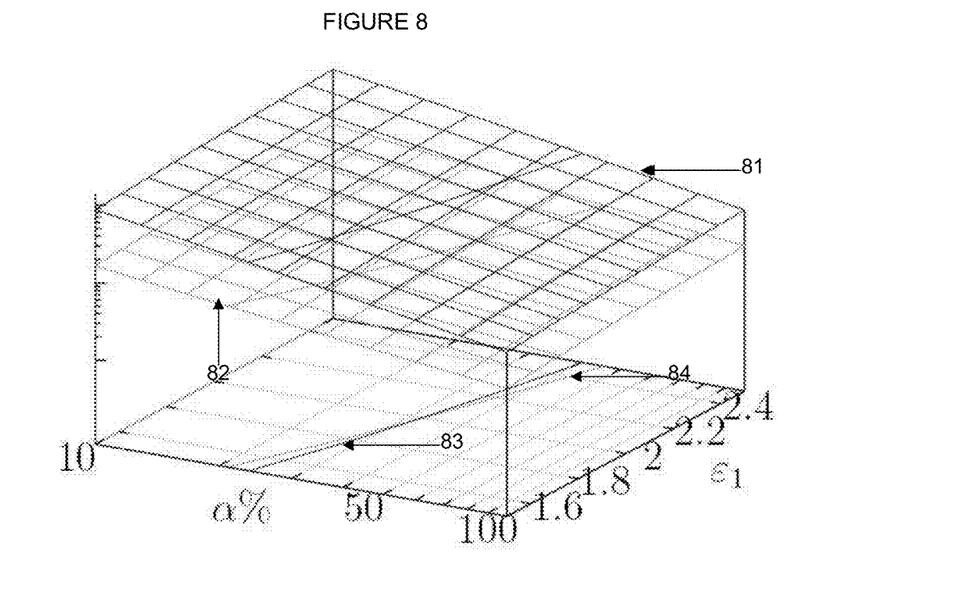
FIG. 8 is a contour plot of the capacitance in the second sensor region of the multiphase meter of FIG. 5 as a function of the composition ratio and the permittivity of the oil.
Figure 9:
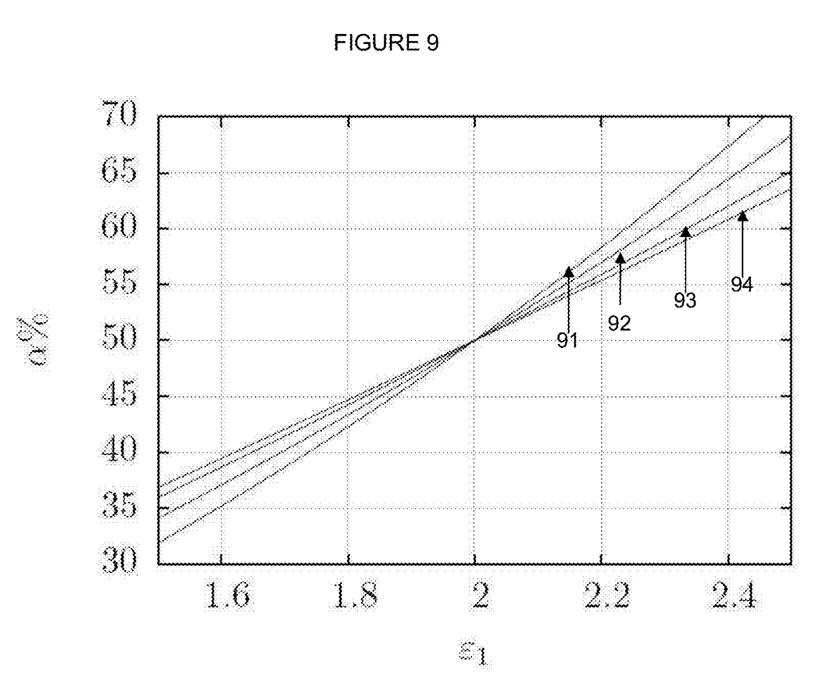
FIG. 9 is a graph showing, for the multiphase meter of FIG. 5 having the ratios of second inner radius to first inner radius shown, that the meter is capable of determining composition ratio and permittivity of the subject fluids.

The following parameters are used to demonstrate the above equation in an oil water mixture, and the results are plotted in FIGS. 7, 8 and 9. (These same parameters are used again for the multiphase meter of FIG. 10.)

$r_1 = 0.01$ [m]
$R_1 = 0.05$ [m]
$r_2 = 2, 4, 8 \cdot r_1$
$(\in_0 A) = 1$ [Fm] to simplify the calculation of $C_i$
$\in_1 \in \{1.5, 2, 5\}$ drifting permittivity (oil)
$\in_2 = 80$ constant permittivity (water)
$\alpha \in \{0\%, 100\%\}$ variable multiphase composition FIG. 7 shows the logarithmic plot of capacitance (y-axis) over water-cut (x-axis) for the sensor of FIG. 5, where the permittivity of the oil is 2 and the inner radius of the second sensor region is 8 times the inner radius of the first sensor region. Curve (71) is the capacitance curve for the first sensor region and curve (72) is the capacitance curve for the second sensor region.

The mixture percentage $\alpha$ % and the permittivity $\in_2$ is derived through the following process. First, capacitances $C_1$ and $C_2$ are measured. Then, two contours $\alpha_{1,2} = \alpha_{1,2}(\in_1)$ associated with each corresponding capacitance $C_{1,2}$ are derived as $$\alpha_i = \frac{\left[\frac{\varepsilon_0\varepsilon_1\varepsilon_2 A}{C_i} - \varepsilon_1 R_i + \varepsilon_2 r_i\right]^2 - (\varepsilon_2 - \varepsilon_1)^2 r_1^2}{(\varepsilon_2 - \varepsilon_1)^2 (R_i^2 - r_i^2)} \qquad \text{Eq. (9)}$$

FIG. 8 illustrates these contours for the given parameters. The two new characteristics must be linearly independent in order to extract the desired parameters $\alpha$ and $\in_1$. In another words, the two contours (81) and (82) projected into the plane $\alpha \angle \in_1$ as lines (83) and (84) respectively, must actually intersect each other (as FIG. 8 shows to be the case). FIG. 9 illustrates this process using idealized data for the $r_1$ value, shown as line (91), and the three $r_2$ values proposed above, shown as line (92) for $r_2=2r_1$; line (93) for $r_2=4r_1$; and line (94) for $r_2=8r_1$.

In FIG. 10, the sensor (100) of the present invention is considered using the piece-wise smooth funnel shaped cyclone (also shown in FIG. 3), with the outer wall (101) and inner wall (102) fitted with concentric ring electrodes (111) and (112) at region #1 and (113) and (114) at region #2, respectively. The input fluid flows in a generally cyclonic direction (103) about the axis (105) from the input to the output (104).

By applying the analysis used in respect of sensor (500) of FIG. 5, a higher degree of linear independence for similar ratios between $r_1$ and $r_2$ can be shown for a sensor (100) of FIG. 10, which suggests a more robust design.

Adopting the same conventions and indexing format from the previous model analysis, the partial capacitances $C_i^1$ and $C_i^2$ can be calculated as $$C_i^1 = \frac{2\pi\varepsilon_0\varepsilon_1 h}{\ln\frac{\rho_i}{r_i}}, \ldots C_i^2 = \frac{2\pi\varepsilon_0\varepsilon_2 h}{\ln\frac{R_i}{\rho_i}}, \quad i = 1, 2 \qquad \text{Eq. (4')}$$

where h is the height of the electrodes. The total capacitances $C_i$ evaluated to $$C_i = \frac{2\pi\varepsilon_0\varepsilon_1\varepsilon_2 h}{\ln R_i^{\varepsilon_1} r_i^{-\varepsilon_2} \rho_i^{\varepsilon_2-\varepsilon_1}} \qquad \text{Eq. (5')}$$

or equivalently in terms of the composition $\alpha$ to $$C_i = \frac{2\pi\varepsilon_0\varepsilon_1\varepsilon_2 h}{\ln\left\{R_i^{\varepsilon_1} r_i^{-\varepsilon_2}[\alpha(R_i^2 - r_i^2) + r_i^2]^{\frac{\varepsilon_2-\varepsilon_1}{2}}\right\}} \qquad \text{Eq. (8')}$$

The two contours $\alpha_{1,2}=\alpha_{1,2}(\in_1)$ associated with each corresponding capacitance $C_{1,2}$ are therefore $$\alpha_i = \frac{\left[R_i^{-\varepsilon_1} r_i^{\varepsilon_2} \exp\left(\frac{2\pi\varepsilon_0\varepsilon_1\varepsilon_2 h}{C_i}\right)\right]^{\frac{2}{\varepsilon_2-\varepsilon_1}} - r_1^2}{(R_i^2 - r_i^2)} \qquad \text{Eq. (9)}$$

Figure 11:
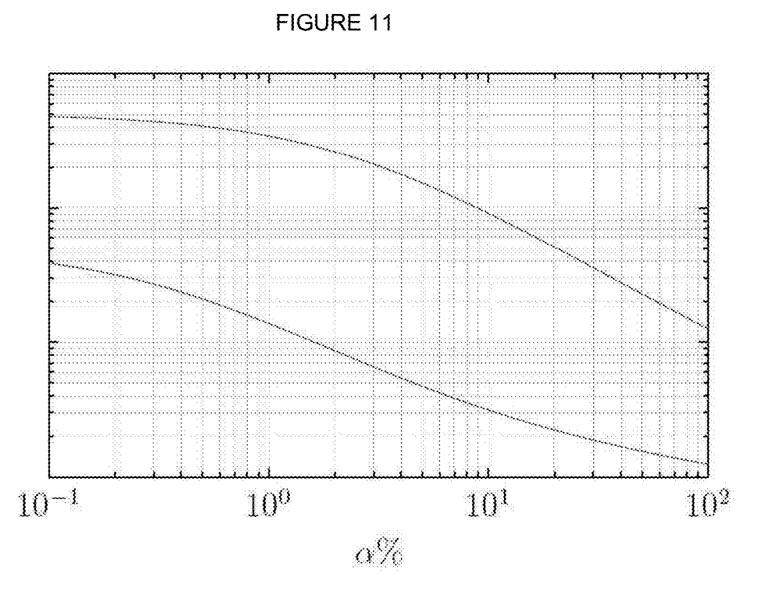
FIG. 11 is a logarithmic plot of capacitances across two sensor regions of the multiphase meter of FIG. 10, as a function of composition, where the ratio of the inner radius of the first sensor region to the inner radius of the second sensor region is 1:8.
Figure 12:
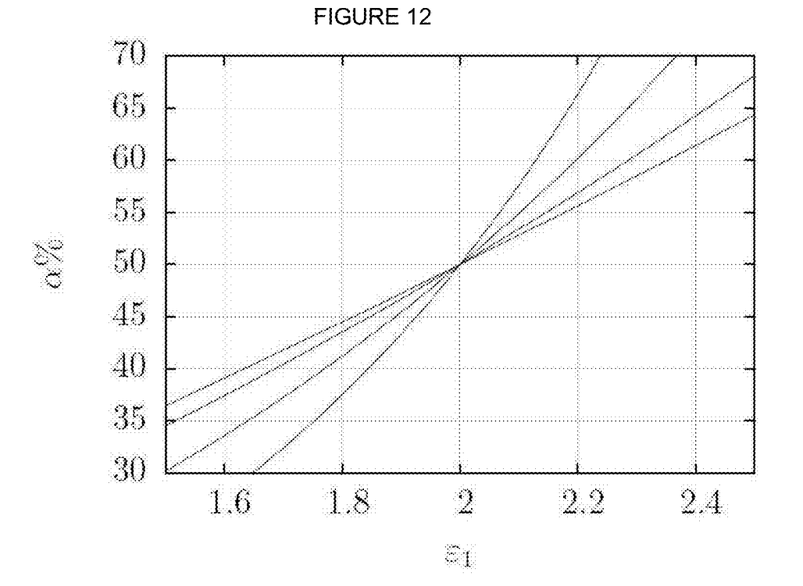
FIG. 12 is a graph showing, for the multiphase meter of FIG. 10 having the ratios of second inner radius to first inner radius shown, that the meter is capable of determining composition ratio and permittivity of the subject fluids.

FIG. 11 is the logarithmic plot for the concentric ring diode computation for the sensor (100) of FIG. 10 which corresponds to the plot in FIG. 7 for the sensor (500) of FIG. 5, using the same input parameters. Similarly, FIG. 12 shows the intersection of the contours projected into the plane $\alpha \angle \in_1$ for sensors (100) of FIG. 10 having three different radii which corresponds to the plots in FIG. 9 for sensors (500) of FIG. 5, using the same input parameters. Comparing the characteristics of linear independence in FIG. 9 and FIG. 12 in terms of three different ratios of radii $r_1$ and $r_2$. The wider angle of intersection indicates a more robust sensor design, but both demonstrate preferred and workable embodiments of the present invention.

The device of the present invention may also be a sensor comprising a measurement chamber of a funnel shape that contains a solid coaxial conic core. One or more testable properties of a multiphase composition (of the forms noted above) are measured across annuli between the outer wall and inner wall, which annuli have different inner and outer radii so as to render the capacitance measurements linearly independent. Although the present disclosure example solves the equations only for 2 sensor regions, the device is scalable to permit additional measurement. As a result, a person of skill in the art would appreciate how the sensor can also be temperature-compensating and self-calibrating. The sensor operates without diverting the flow or using nuclear particles, as is therefore non-mixing and environmentally-neutral.

The present invention may also feature a conic non-conductive core bearing a stack of surface mounted, possibly insulated ring electrodes (measuring and guard electrodes) that establish an AC electrostatic field in the annuli cavities in relation to a funnel-shaped global metallic electrode outer wall which serves as a common reference voltage (possibly ground). The electro-magnetic field measurements at various frequencies and/or phase variations for such a system would be extremely robust.

In yet another embodiment, a stack of independent coils can be also utilized in the measurement of self- and/or mutual-inductances along the funnel shaped chamber. An intermediate measure and (capacitance/conductance/self-/mutual-inductance) detected at each discrete measuring location (electrode/coil) is a function of, inter alia, the following parameters: the phase volumetric fraction(s); materials' constants, including individual phase permittivities/conductances/permeabilities; the physical dimensions of the sensor chamber; pick-up elements, including electrode area/number of coil turns and inter-electrode/coil spacing); and temperature. The proximity of the multiple measuring locations (i.e. electrodes or coils) must be relatively small for flows where rapidly varying compositions are present.

Gravity may be used to improve uniformity of the radial stratification by orienting the axis of the funnel shaped sensor chamber vertically. Depending on how much mixing is permitted, radial pressure to facilitate stratification may also be increased by increasing the fluid velocity by way of impellers, recirculation pumps, etc.

A multiphase composition meter of the present invention using a capacitive sensor array is particularly suitable for applications where conventional phase-mixing (homogenous flow), radiation absorption (X-ray, gamma-ray, micro-waves) type meters cannot be used, or would imply the non-ideal use of a complex, expensive and/or environmentally unfriendly phase separation process downstream of the meter. The meter of the present invention employs a non-mixing (non-emulsifying) process in which the individual phases, if available, are stratified into a layered flow which makes it ideal for measuring a composition of raw materials, such as oil-water-gas flows, or processes that involve a phase separation. In a preferred embodiment, the meter does not require a field-calibration which is advantageous in subsea or marginal field installations.

A skilled practitioner would be aware of additional assistance in solving these equations available in "Efficient method for the capacitance calculation of circularly symmetric via in multilayered media", Tefiku, F.; Yamashita, E., Microwave and Guided Wave Letters, IEEE, Volume 5, Issue 9, September 1995 Page(s): 305-307 Digital Object Identifier 10.1109/75.410406; and Industrial Process Control: Advances and Applications, Gulf Professional Publishing; 1 ed. (2002), pp. 33 (Ch. 2.6 Multiphase Flow Metering), ISBN-13: 978-0750674461

The foregoing embodiments and advantages are merely exemplary and are not to be construed as limiting the present invention. The present teaching can be readily applied to other types of apparatuses. Also, the description of the embodiments of the present invention is intended to be illustrative, and not to limit the scope of the claims, and many alternatives, modifications, and variations will be apparent to those skilled in the art.

The invention claimed is:

1. A sensor chamber for use in determining composition of a multiphase fluid, comprising:
   a. A chamber wall having known curvature about a chamber axis;
   b. A sensor chamber input at a first end of the sensor chamber, oriented to encourage cyclonic motion of the multiphase fluid about the chamber wall in a direction around the chamber axis so as to create a centripetal force to locally stratify the multiphase fluid in centripetal force directions;
   c. A sensor chamber output at a second end of the sensor chamber along the chamber axis from the sensor chamber input; and
   d. A first sensor region located between the sensor input and the sensor output and defined by a first chamber wall segment across which the multiphase fluid is to be radially stratified in the centripetal force direction by the centripetal force imparted by the cyclonic motion.

2. The sensor chamber of claim 1 further comprising a second sensor region between the sensor input and the sensor output of different shape from the first sensor region and defined in part by a second chamber wall segment across which the multiphase fluid is to be radially stratified in the centripetal force direction by the centripetal force imparted by the cyclonic motion.

3. The sensor chamber of claim 1 further comprising a concentric core on the chamber axis, the surface of the concentric core being an inner wall of the sensor chamber, the first sensor region further defined as the volume between the first chamber wall segment and a corresponding first inner wall segment of the inner wall between the first chamber wall segment and the sensor axis.

4. The sensor chamber of claim 2 further comprising a concentric core on the chamber axis, the surface of the concentric core being an inner wall of the sensor chamber, the first sensor region further defined as the volume between the first chamber wall segment and a corresponding first inner wall segment of the inner wall between the first chamber wall segment and the sensor axis and the second sensor region further defined as the volume between the second chamber wall segment and a corresponding second inner wall segment of the inner wall between the second chamber wall segment and the sensor axis.

5. The sensor chamber of claim 4 wherein the chamber axis, from the sensor chamber input to the sensor chamber output, is substantially in the direction of gravity so as to increase the centripetal force.

6. The sensor chamber of claim 4 connected to a recirculating pump to increase flow velocity of the multiphase fluid within the sensor chamber so as to increase the centripetal force.

7. A sensor to measure composition of a multiphase fluid, comprising:
   a. A sensor chamber comprising
      i. A chamber wall having known curvature about a chamber axis;
      ii. A sensor chamber input at a first end of the sensor chamber, oriented to encourage cyclonic motion of the multiphase fluid about the chamber wall in a cyclonic direction around the chamber axis so as to create a centripetal force to locally stratify the multiphase fluid in centripetal force directions substantially perpendicular to the curvature of the chamber wall;
      iii. A sensor chamber output at a second end of the sensor chamber along the chamber axis from the sensor chamber input;
      iv. A plurality of sensor regions located between the sensor input and the sensor output and each defined by a chamber wall segment across which the multiphase fluid is to be radially stratified in the centripetal force direction by the centripetal force imparted by the cyclonic motion, and each sensor region having a distinct shape; and
   b. A plurality of sensor elements, at least one at each sensor region, to measure at least one property of the multiphase fluid in the direction of the centripetal force.

8. The sensor of claim 7 wherein the sensor chamber further comprises a concentric core on the chamber axis, the surface of the concentric core being an inner wall of the sensor chamber, at least one of the plurality of sensor regions further defined as the volumes between such chamber wall segments and at least one corresponding inner wall segment of the inner wall between such chamber wall segments and the sensor axis.

9. The sensor of claim 7 wherein the at least one property of the multiphase fluid is a property from the group of properties consisting of: speed of propagation of ultrasonic waves; amplitude modulation of ultrasonic waves, attenuation of ultrasonic waves, X-rays, gamma rays, microwaves, infrared, visible and ultraviolet light; phase modulation or standing wave resonance of ultrasonic waves and microwaves; spin states of nuclei of nuclear magnetic resonance; and complex impedance, capacitance, inductance, mutual inductance, conductance, frequency response and phase delay.

10. The sensor of claim 8 wherein the at least one property of the multiphase fluid is a property from the group of properties consisting of: speed of propagation of ultrasonic waves; amplitude modulation of ultrasonic waves, attenuation of ultrasonic waves, X-rays, gamma rays, microwaves, infrared, visible and ultraviolet light; phase modulation or standing wave resonance of ultrasonic waves and microwaves; spin states of nuclei of nuclear magnetic resonance; and complex impedance, capacitance, inductance, mutual inductance, conductance, frequency response and phase delay.

11. The sensor of claim 10 wherein at least one property of the multiphase fluid is capacitance and at least two of the sensor array elements are parallel plate electrodes acting as a pair on the chamber wall segment and inner wall segment of the same sensor region.

12. The sensor of claim 10 wherein at least one property of the multiphase fluid is capacitance and at least two of the sensor array elements are parallel ring electrodes acting as a pair on the chamber wall segment and inner wall segment of the same sensor region.

13. The sensor of claim 10 wherein the at least one property of the multiphase fluid is mutual inductance and the sensor array elements are parallel coil electrodes acting as a pair through the chamber wall segment and inner wall segment of the same sensor region.

14. The sensor of claim 10 wherein the chamber axis, from the sensor chamber input to the sensor chamber output, is substantially in the direction of gravity so as to increase the centripetal force.

15. The sensor of claim 10 connected to a recirculating pump to increase flow velocity of the multiphase fluid within the sensor chamber so as to increase the centripetal force.

16. The sensor of claim 10 further comprising computation means for receiving signals representing estimates of the properties from the plurality of sensor regions and using such signals to estimate the composition of the multiphase fluid based on such properties, the sensor array and the geometry of the sensor chamber.

17. A sensor for determining composition of a multiphase fluid comprising
   a. One or more sensor chambers, themselves each comprising:
      i. a chamber wall having a known curvature about a chamber axis to impart a centripetal force on the multiphase fluid in centripetal force directions substantially perpendicular to the known curvature and substantially radial from the chamber axis;
      ii. A sensor chamber input through the chamber wall to provide fluid communication into the sensor chamber at a first end of the sensor chamber, the sensor chamber input oriented to impart cyclonic motion on the multiphase fluid;
      iii. A sensor chamber output in the direction of the chamber axis, away from the sensor chamber input;
      iv. At least one first sensor region located between the sensor input and the sensor output and defined by a first chamber wall segment across which the multiphase flow is to be radially stratified by the centripetal force, such that sensors adapted for use with such sensor chamber can measure one or more first parameters of the multiphase flow across such radially stratified flow;
   b. At least one second sensor region located between the sensor input and the sensor output of one of the sensor chambers, which second sensor region is of different shape from the first sensor region and defined in part by a second chamber wall segment across which the multiphase fluid is to be radially stratified by such centripetal force imparted by such sensor chamber, such that sensors adapted for use with such sensor chamber can measure one or more second parameters of the multiphase flow across such radially stratified flow;
   c. A sensor array having a first sensor in the first sensor region for measuring the one or more first parameters in the centripetal force directions in such first sensor region and a second sensor in the second sensor region for measuring the one or more second parameters in the centripetal force directions in such second sensor region; and
   d. Computation means for receiving signals representing the first parameter and the second parameter and using such signals to estimate the composition of the multiphase flow based on the first parameter and the second parameter.

18. The sensor of claim 17 further comprising:
   a. a third sensor region between the sensor input and the sensor output of the one or more sensor chambers of different shape from either the first sensor region or the second sensor region and defined in part by a third chamber wall segment across which the multiphase fluid is radially stratified by the centripetal force such that a third parameter measured across the third sensor region is linearly independent of the one or more first parameters and the one or more second parameters;
   b. the sensor array further comprising a third sensor for measuring the third parameter; and
   c. the computation means computing the composition of the multiphase fluid based on relationships between the one or more first parameters, the one or more second parameters, the third parameter, the geometries of the sensors chamber and the sensor array and calibration values based on a database of expected parameter values for the multiphase flow.

19. The sensor of claim 17 further comprising tapering within at least one of the sensor chamber to narrow the cross sectional area of the region bounded chamber wall between the sensor chamber input and the sensor chamber output.

20. The sensor of claim 19 further comprising a concentric core on the chamber axis of at least one of the sensor chambers, the surface of the concentric core being an inner wall of the sensor chamber, the concentric core shaped to maintain substantially equal cross sectional area in the region bounded between the chamber wall and the inner wall in the direction of flow from the sensor chamber input to the sensor chamber output of such sensor chamber.

* * * * *